(12) United States Patent
Machida

(10) Patent No.: US 8,012,084 B2
(45) Date of Patent: Sep. 6, 2011

(54) ENDOSCOPE DEVICE AND CONTROL METHOD FOR THE SAME

(75) Inventor: Mitsunori Machida, Saitama (JP)

(73) Assignee: Fiujinon Corporation, Saitama-shi (JP)

( * ) Notice: Subject to any disclaimer, the term of this patent is extended or adjusted under 35 U.S.C. 154(b) by 945 days.

(21) Appl. No.: 11/268,510

(22) Filed: Nov. 8, 2005

(65) Prior Publication Data

US 2006/0111610 A1 May 25, 2006

(30) Foreign Application Priority Data

Nov. 9, 2004 (JP) ................................ P.2004-324914

(51) Int. Cl.
*A61B 1/00* (2006.01)

(52) U.S. Cl. ........ 600/115; 600/114; 600/116; 600/121; 604/96.01; 604/101.01; 604/101.02

(58) Field of Classification Search .......... 600/115–116; 604/96.01–103
See application file for complete search history.

(56) References Cited

U.S. PATENT DOCUMENTS

| | | | | |
|---|---|---|---|---|
| 4,040,413 A * | 8/1977 | Ohshiro | | 600/116 |
| 4,224,929 A * | 9/1980 | Furihata | | 600/116 |
| 4,295,464 A * | 10/1981 | Shihata | | 606/127 |
| 4,862,874 A * | 9/1989 | Kellner | | 600/116 |
| 4,911,163 A * | 3/1990 | Fina | | 606/127 |
| 5,024,658 A * | 6/1991 | Kozlov et al. | | 604/101.04 |
| 5,222,970 A * | 6/1993 | Reeves | | 606/195 |
| 5,779,672 A * | 7/1998 | Dormandy, Jr. | | 604/99.04 |
| 5,938,585 A * | 8/1999 | Donofrio | | 600/115 |
| 6,007,482 A | 12/1999 | Madni et al. | | |
| 6,126,635 A * | 10/2000 | Simpson et al. | | 604/101.05 |
| 6,135,981 A * | 10/2000 | Dyke | | 604/96.01 |
| 6,234,958 B1 * | 5/2001 | Snoke et al. | | 600/114 |
| 6,471,654 B2 * | 10/2002 | Ohara et al. | | 600/463 |
| 6,585,639 B1 * | 7/2003 | Kotmel et al. | | 600/116 |
| 6,702,735 B2 * | 3/2004 | Kelly | | 600/115 |
| 6,740,082 B2 * | 5/2004 | Shadduck | | 606/41 |
| 6,821,263 B2 * | 11/2004 | Lenker et al. | | 604/4.01 |
| 6,988,987 B2 * | 1/2006 | Ishikawa et al. | | 600/114 |
| 7,591,782 B2 * | 9/2009 | Fujikura | | 600/116 |
| 2002/0143237 A1 * | 10/2002 | Oneda et al. | | 600/116 |
| 2003/0093105 A1 | 5/2003 | Huffmaster | | |
| 2004/0186349 A1 * | 9/2004 | Ewers et al. | | 600/114 |
| 2004/0249243 A1 * | 12/2004 | Kleiner | | 600/115 |
| 2005/0059931 A1 * | 3/2005 | Garrison et al. | | 604/101.04 |
| 2005/0065468 A1 * | 3/2005 | Goebel | | 604/96.01 |
| 2005/0113799 A1 * | 5/2005 | Lenker | | 604/509 |
| 2005/0159645 A1 * | 7/2005 | Bertolero et al. | | 600/116 |

FOREIGN PATENT DOCUMENTS

EP 1 547 641 A2 6/2005

(Continued)

*Primary Examiner* — Matthew J Kasztejna

(74) *Attorney, Agent, or Firm* — Birch, Stewart, Kolasch & Birch, LLP

(57) ABSTRACT

An endoscope device comprises: an endoscope including an insertion portion and a first balloon attached to a distal end of the insertion portion; and an insertion guide that is to be covered on the insertion portion to guide insertion of the insertion portion, the insertion guide comprising a second balloon on its distal end, wherein the insertion portion or the insertion guide is fixed in a body cavity by expanding the first balloon or the second balloon, respectively, wherein the first balloon and the second balloon are substantially equal to each other in friction resistance against the body cavity when they are expanded.

11 Claims, 4 Drawing Sheets

FOREIGN PATENT DOCUMENTS

| | | |
|---|---|---|
| JP | 51-11689 A | 1/1976 |
| JP | 8-89476 A | 4/1996 |
| JP | 11-290263 A | 10/1999 |
| JP | 11290263 A | 10/1999 |
| JP | 2001-340462 A | 12/2001 |

* cited by examiner

ENDOSCOPE DEVICE AND CONTROL METHOD FOR THE SAME

BACKGROUND OF THE INVENTION

1. Field of the Invention

The present invention relates to an endoscope device and a control method for the same, and more specifically, an endoscope device to be used for observation of deep digestive tracts such as the small intestine and the colon, and a control method for the same.

2. Description of the Related Art

When an insertion portion of an endoscope is inserted in a deep digestive tract such as the small intestine, if the insertion portion is only pushed and inserted, it is difficult to transmit the pushing force to the distal end of the insertion portion due to complicated bends of the intestinal tract, and insertion to a deep portion is difficult. For example, when the insertion portion unnecessarily bends or warps, it becomes impossible to insert the insertion portion to a deeper side. Therefore, a method for preventing unnecessary bending and warping of the insertion portion of an endoscope by guiding the insertion portion by an insertion guide that is covered on the insertion portion and inserted in the body cavity has been proposed.

For example, JP-A-51-11689 and JP-A-11-290263 describe endoscope devices provided with a first balloon on the distal end of the insertion portion of the endoscope and a second balloon on the distal end of an insertion guide (referred to as overtube or sliding tube, also). The first balloon and the second balloon can fix the insertion portion and the insertion guide in an intestinal tract such as the small intestine by being expanded. Therefore, by alternately inserting the insertion portion and the insertion guide while repeating expansion and contraction of the first balloon and the second balloon, the insertion portion can be inserted to a deep portion of a complicatedly bent intestinal tract such as the small intestine.

However, the endoscope devices of JP-A-51-11689 and JP-A-11-290263 have a possibility that when the two balloons are expanded and the insertion portion and the insertion guide are pushed or pulled, the balloons pressurize the intestinal wall and impose a heavy burden on the intestinal tract. Therefore, the friction resistances between the balloons being expanded and the intestinal tract are important, however, neither of JP-A-51-11689 and JP-A-11-290263 disclose this.

SUMMARY OF THE INVENTION

The invention was made in view of these circumstances, and an object thereof is to provide an endoscope device and a control method for the same which can reduce the burden on the body cavity from balloons.

According to a first aspect of the invention, to achieve the object, there is provided an endoscope device comprising: an endoscope including an insertion portion and a first balloon attached to a distal end of the insertion portion; and an insertion guide that is to be covered on the insertion portion to guide insertion of the insertion portion, the insertion guide comprising a second balloon on its distal end, wherein the insertion portion or the insertion guide is fixed in a body cavity by expanding the first balloon or the second balloon, respectively, wherein the first balloon and the second balloon are substantially equal to each other in friction resistance against the body cavity when they are expanded.

According to the first aspect of the invention, since the first balloon and the second balloon have the same friction resistance against the body cavity when they are expanded, when both balloons are expanded and the insertion portion and the insertion guide are pushed or pulled, the balloons can be prevented from pressurizing the body cavity. In addition, both balloons can be set to have a friction resistance that makes the balloons least likely to damage the body cavity and to be securely fixed in the body cavity.

According to a second aspect of the invention, in the first aspect of the invention, the first balloon and the second balloon comprise materials that are substantially equal to each other in friction resistance against the body cavity. Therefore, according to the second aspect of the invention, the friction resistance becomes equal between the first balloon and the second balloon when they are expanded.

According to a third aspect of the invention, in the first or second aspect of the invention, the first balloon and the second balloon comprise materials that are substantially equal to each other in coefficient of expansion. Therefore, according to the third aspect of the invention, the first balloon and the second balloon can be expanded to the same size regardless of the internal pressures of the balloons. Therefore, the friction resistances when the balloons are expanded can be made equal to each other between the first balloon and the second balloon.

According to a fourth aspect of the invention, in the invention of any one of the first to third aspects of the invention, wherein the first balloon and the second balloon are substantially equal to each other in area to contact with the body cavity when they are expanded. According to the fourth aspect of the invention, the balloons are equal to each other in contact areas, so that their friction resistances become equal to each other when the insertion portion or the insertion guide is pushed or pulled.

To achieve the object, according to a fifth aspect of the invention, there is provided a control method for an endoscope device, in which the endoscope device comprises: an endoscope including an insertion portion and a first balloon attached to a distal end of the insertion portion; and an insertion guide that is to be covered on the insertion portion to guide insertion of the insertion portion, and the insertion guide comprises a second balloon on its distal end, the method comprising fixing the endoscope device in a body cavity by using the first balloon and the second balloon that become substantially equal to each other in friction resistance against the body cavity when they are expanded.

According to the fifth aspect of the invention, the first balloon and the second balloon becomes equal to each other in friction resistance against the body cavity when they are expanded, so that when the balloons are expanded and the insertion portion and the insertion guide are pushed or pulled, the balloons can be prevented from pressurizing the body cavity. In addition, the balloons can be set to have a friction resistance that makes the balloons least likely to damage the body cavity and to be securely fixed in the body cavity.

DETAILED DESCRIPTION OF THE INVENTION

Figure 1:
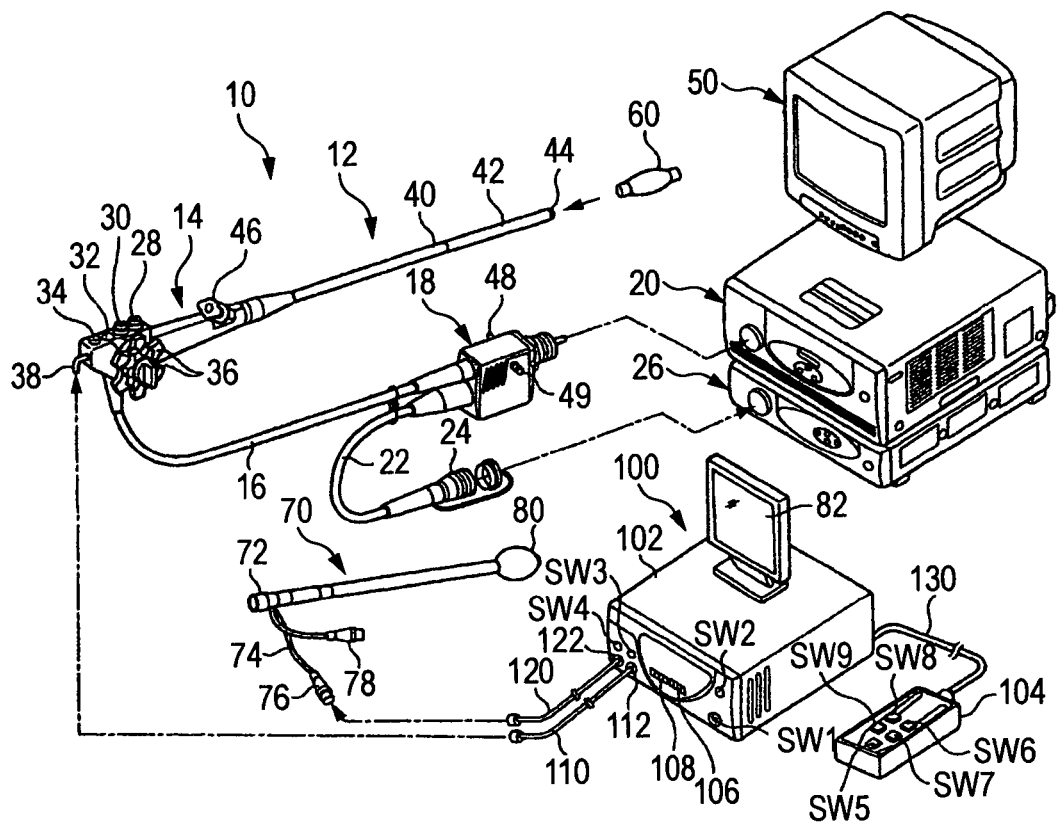
FIG. 1 is a system constructional diagram of an endoscope device according to the invention.

Hereinafter, an endoscope device and a control method for the same according to the invention are described in detail with reference to the accompanying drawings. FIG. 1 is a system constructional diagram of an embodiment of an endoscope device according to the invention. As shown in FIG. 1, the endoscope device mainly comprises an endoscope 10, an insertion guide 70, and a balloon controller 100.

As shown in FIG. 1, the endoscope 10 has a hand-side control portion 14, and an insertion portion 12 that is continued from the hand-side control portion 14 and is to be inserted into a body cavity. To the hand-side control portion 14, a universal cable 16 is connected, and on the distal end of this universal cable 16, an LG connector 18 is provided. The LG connector 18 is detachably linked to a light source device 20, whereby illumination light is supplied to an illumination optical system 54 (see FIG. 2) described later. In addition, to the LG connector 18, an electrical connector 24 is connected via a cable 22, and this electrical connector 24 is detachably linked to a processor 26.

At the hand-side control portion 14, an air/water button 28, a suction button 30, a shutter button 32, and a function switching button 34 are provided together, and a pair of angle knobs 36 and 36 are provided. On the base end of the hand-side control portion 14, a balloon air inlet 38 is formed of an L-bent tube. By supplying or suctioning a fluid such as the air to or from this balloon air inlet 38, the first balloon 60 that is described later can be expanded or contracted.

The insertion portion 12 comprises, in order from the hand-side control portion 14 side, a flexible portion 40, a bending portion 42, and a distal end portion 44, and the bending portion 42 is remote-controlled to bend by rotating the angle knobs 36 and 36 on the hand-side control portion 14. Thereby, the distal end portion 44 can be turned to a desired direction.

Figure 2:
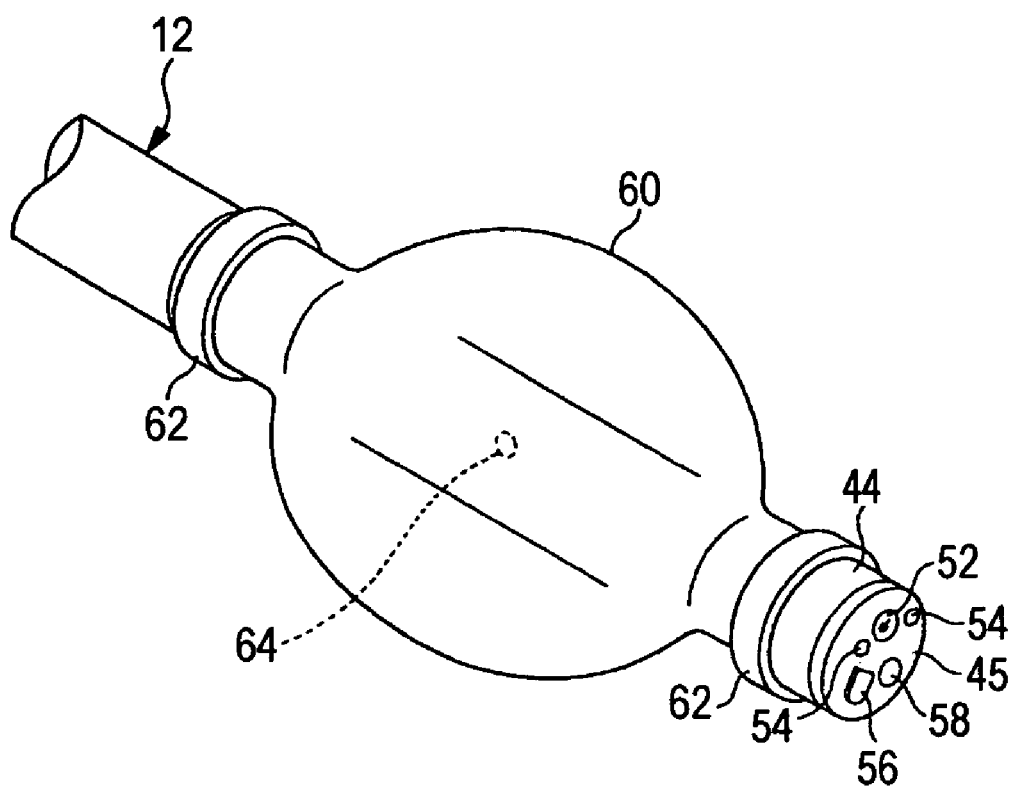
FIG. 2 is a perspective view of a distal end of an insertion portion of an endoscope.

As shown in FIG. 2, on the distal end face 45 of the distal end portion 44, an observation optical system 52, illumination optical systems 54 and 54, an air/water nozzle 56, and a forceps opening 58 are provided. At the rear of the observation optical system 52, a CCD (not shown) is disposed, and a signal cable (not shown) is connected to a substrate supporting this CCD. The signal cable is inserted through the insertion portion 12, the hand-side control portion 14, the universal cable 16, and so on of FIG. 1 and extended to the electrical connector 24, and connected to the processor 26. Therefore, an observation image taken by the observation optical system 52 is formed on a light receiving surface of the CCD and converted into an electrical signal, and this electrical signal is outputted to the processor 26 via the signal cable and converted into a video signal. Thereby, the observation image is displayed on a monitor 50 connected to the processor 26.

At the rear of the illumination optical systems 54 and 54 of FIG. 2, an exit end of a light guide (not shown) is disposed. This light guide is inserted through the insertion portion 12, the hand-side control portion 14, and the universal cable 16 of FIG. 1, and its incidence end is disposed inside the LG connector 18. Therefore, by linking the LG connector 18 to the light source device 20, illumination light irradiated from the light source device 20 is transmitted to the illumination optical systems 54 and 54 via the light guide, and irradiated forward from the illumination optical systems 54 and 54.

The air/water nozzle 56 of FIG. 2 is communicated with a valve (not shown) that is controlled by the air/water button 28 of FIG. 1, and this valve is communicated with an air/water connector 48 provided in the LG connector 18. The air/water connector 48 is connected to an unillustrated air/water feed means, whereby air or water is supplied. Therefore, by operating the air/water button 28, air or water can be jetted toward the observation optical system 52 from the air/water nozzle 56 of FIG. 2.

The forceps opening 58 of FIG. 2 is communicated with a forceps insertion portion 46 of FIG. 1. Therefore, by inserting treatment equipment such as forceps from the forceps insertion portion 46, this treatment equipment can be led out from the forceps opening 58. The forceps opening 58 is communicated with a valve (not shown) that is controlled by the suction button 30 of FIG. 1, and this valve is further connected to a suction connector 49 of the LG connector 18. Therefore, by connecting an unillustrated suction means to the suction connector 49 and controlling the valve by the suction button 30, a lesion portion or the like can be suctioned from the forceps opening 58.

To the outer circumferential surface of the insertion portion 12, a first balloon 60 made of an elastic material such as rubber is attached. The first balloon 60 is formed into a roughly cylindrical shape narrowed on both ends, and after the insertion portion 12 is inserted through the first balloon 60 and the first balloon is disposed at a desired position, as shown in FIG. 2, fixing rings 62 and 62 made of rubber are fitted on both ends of the first balloon 60, whereby the first balloon 60 is fixed to the insertion portion 12.

In the outer circumferential surface of the insertion portion 12 where the first balloon 60 is attached, a vent hole 64 is formed. The vent hole 64 is communicated with the balloon air inlet 38 formed in the hand-side control portion 14 of FIG. 1, and the balloon air inlet 38 is connected to the balloon controller 100 via a tube 110 described later. Therefore, by supplying or suctioning air by the balloon controller 100, the first balloon 60 can be expanded and contracted. The first balloon 60 is expanded into a roughly spherical shape by supplying air into it, and adheres to the outer surface of the insertion portion 12 by suctioning air from it.

On the other hand, the insertion guide 70 shown in FIG. 1 is formed into a cylindrical shape, and has an inner diameter slightly larger than the outer diameter of the insertion portion 12 and sufficient flexibility. On the base end of the insertion guide 70, a hard gripping portion 72 is provided, and from this gripping portion 72, the insertion portion 12 is inserted.

Near the distal end of the insertion guide 70, a second balloon 80 is attached. The second balloon 80 is formed into a roughly cylindrical shape narrowed at both ends, and is attached while the insertion guide 70 is inserted therein, and fixed by winding a thread that is not shown. A tube 74 adhering to the outer circumferential surface of the insertion guide 70 is communicated with the second balloon 80, and at the base end of this tube 74, a connector 76 is provided. A tube 120 is connected to the connector 76, and the connector is connected to the balloon controller 100 via this tube 120. Therefore, by supplying and suctioning air by the balloon controller 100, the second balloon 80 can be expanded and contracted. The second balloon 80 is expanded into a roughly spherical shape by supplying air into it, and adheres to the outer circumferential surface of the insertion guide 70 by suctioning air from it.

On the base end side of the insertion guide 70, an injection port 78 is provided. This injection port 78 is communicated with an opening (not shown) formed in the inner circumferential surface of the insertion guide 70. Therefore, by injecting a lubricant (for example, water) by a syringe or the like from the injection port, the lubricant can be supplied to the inside of the insertion guide 70. Therefore, when the insertion portion 12 is inserted into the insertion guide 70, the friction between the inner circumferential surface of the insertion guide 70 and the outer circumferential surface of the insertion portion 12 can be reduced, and relative movements of the insertion portion 12 and the insertion guide 70 can be made smooth.

The balloon controller 100 supplies and suctions a fluid such as air into and from the first balloon 60, and supplies and suctions a fluid such as air into and from the second balloon 80. The balloon controller 100 mainly comprises a controller main body 102 and a hand switch 104 for remote control.

On the front face of the controller main body 102, a power source switch SW1, a stop switch SW2, a first pressure display part 106, a second pressure display part 108, a first function stop switch SW3, and a second function stop switch SW4 are provided. The first pressure display part 106 and the second pressure display part 108 are panels for displaying the pressure values of the first balloon 60 and the second balloon 80, and when an abnormality such as a balloon burst occurs, an error code is displayed on the pressure display part 106 or 108. The first function stop switch SW3 and the second function stop switch SW4 are switches for stopping the function of supplying or suctioning to or from the first balloon 60 and the second balloon 80, and are operated when either one of the first balloon 60 or the second balloon 80 is not used.

To the front face of the controller main body 102, a tube 110 for supplying and suctioning air to and from the first balloon 60 and a tube 120 for supplying and suctioning air to and from the second balloon 80 are connected. At the connecting portions between the tubes 110 and 120 and the controller main body 102, reflux preventive units 112 and 122 for preventing reflux of a body fluid when the first balloon 60 or the second balloon 80 bursts are provided. The reflux preventive units 112 and 122 are formed by incorporating a gas-liquid separating filter inside a hollow disk-shaped case (not shown) detachably attached to the controller main body 102, and prevents a liquid from flowing into the controller main body 102 by a filter.

On the other hand, in the hand switch 104, a stop switch SW5 similar to the stop switch SW2 on the controller main body 102 side, an ON/OFF switch SW6 that supports pressurization and decompression of the first balloon 60, a pose switch SW7 for maintaining the pressure of the first balloon 60, an ON/OFF switch SW8 that supports pressurization and decompression of the second balloon 80, and a pose switch SW9 for maintaining the pressure of the second balloon 80 are provided, and this hand switch 104 is electrically connected to the controller main body 102 via a cord 130. The hand switch 104 is provided with a display part that displays the air feed states to the first balloon 60 and the second balloon 80 or exhaust states from these balloons although this display part is not shown in FIG. 1.

The balloon controller 100 thus constructed supplies air to the balloons 60 and 80 to expand these, and controls the air pressures thereof at constant values to keep the expanded states of the balloons 60 and 80. In addition, the balloon controller suctions air from the balloons 60 and 80 to contract these, and keep the contracted states of the balloons 60 and 80 by controlling the air pressures thereof at constant values.

The balloon controller 100 is connected to a balloon exclusive monitor 82, and displays the pressure values and expanded or contracted states of the balloons 60 and 80 on the balloon exclusive monitor 82 when expanding and contracting the respective balloons 60 and 80. It is also allowed that the pressure values and the expanding and contracting states of the balloons 60 and 80 are indicated on a monitor 50 by superimposing these on the observation image of the endoscope 10.

The first balloon 60 and the second balloon 80 are formed so that their friction resistances against the intestinal tract 90 (see FIGS. 3A to 3H) become equal to each other when they are expanded. In detail, when air is supplied and a predetermined internal pressure (for example, 5.6 kPa) is applied to the first balloon 60 and the second balloon 80, the balloons are expanded into spherical shapes having the same size as shown in FIG. 4, and are kept with the same size. Therefore, the friction resistances against the intestinal tract 90 become equal to each other between the first balloon 60 and the second balloon 80. The internal pressures of the balloons 60 and 80 are preferably at values that enable the balloons 60 and 80 to grasp the intestinal tract 90, that is, for example, equal to or more than 26.7 hPa and equal to or less than 133.3 hPa.

A control method for the endoscope device constructed as described above is described with reference to FIG. 3A through FIG. 3H.

Figure 3A:
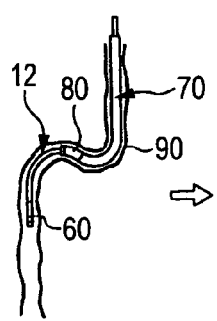
FIGS. 3A to 3H are explanatory views of a control method for an endoscope device according to the invention.
Figure 3B:
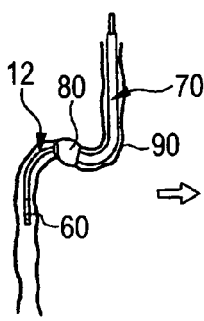
Figure 4:
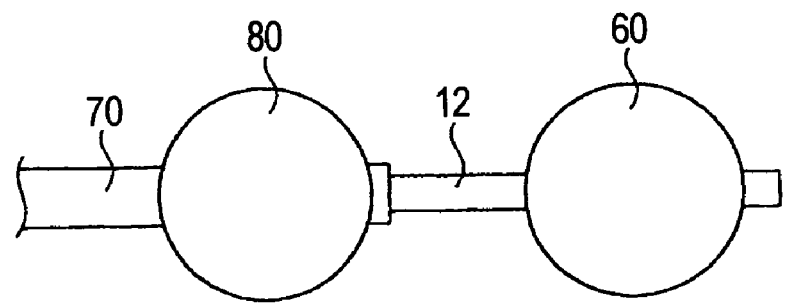
FIG. 4 is a side view of shapes of the balloons of the embodiment when they are expanded.

First, as shown in FIG. 3A, while the insertion guide 70 is covered on the insertion portion 12, the insertion portion 12 is inserted in the intestinal tract 90 (for example, the duodenum descending limb). At this point, the first balloon 60 and the second balloon 80 are contracted in advance.

Next, as shown in FIG. 33, while the distal end of the insertion guide 70 is inserted to the bending portion of the intestinal tract 90, air is supplied to the second balloon 80 to expand this. Thereby, the second balloon 80 is latched on the intestinal tract 90, and the distal end of the insertion guide 70 is fixed to the intestinal tract 90.

Figure 3C:
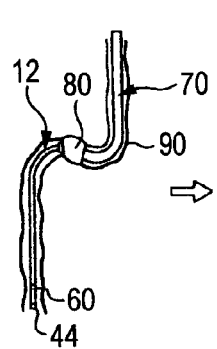
Figure 3D:
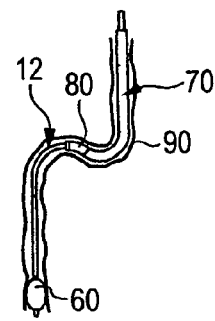

Next, as shown in FIG. 3C, only the insertion portion 12 of the endoscope 10 is inserted to a deep portion of the intestinal tract 90. Then, as shown in FIG. 3D, air is supplied to the first balloon 60 to expand it. Thereby, the first balloon 60 is fixed to the intestinal tract 90.

Figure 3E:
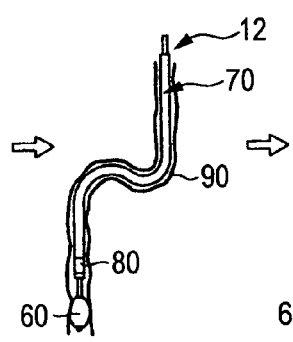
Figure 3F:
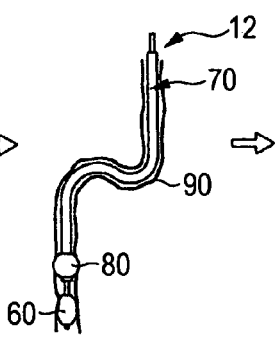

Next, after air is suctioned from the second balloon 80 to contract the second balloon 80, as shown in FIG. 3E, the insertion guide 70 is pushed in and inserted along the insertion portion 12. Then, the distal end of the insertion guide 70 is brought to the vicinity of the first balloon 60, and thereafter, as shown in FIG. 3F, air is supplied to the second balloon 80 to expand it. Thereby, the second balloon 80 is fixed to the intestinal tract 90. Namely, the intestinal tract 90 is grasped by the second balloon 80.

Figure 3G:
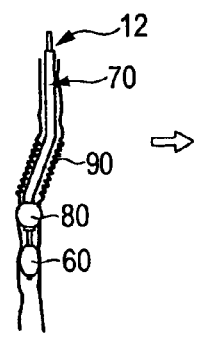
Figure 3H:
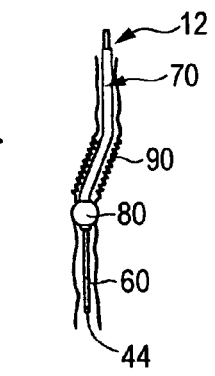

Next, as shown in FIG. 3G, the insertion guide 70 is hauled in. Thereby, the intestinal tract 90 is contracted, and the insertion guide 70 becomes free from unnecessary warping and bending. Next, as shown in FIG. 3H, the first tube 60 is contracted by suctioning air from the first balloon 60. Then, the distal end portion 44 of the insertion portion 12 is inserted to the deepest portion possible in the intestinal tract 90. Namely, the insertion shown in FIG. 3C is performed again. Thereby, the distal end portion 44 of the insertion portion 12 can be inserted to a deep portion in the intestinal tract 90. When the insertion portion 12 is inserted to a deeper portion, after the fixing operation as shown in FIG. 3D is performed, the pushing-in operation as shown in FIG. 3E is performed, and furthermore, the grasping operation as shown in FIG. 3F, the hauling operation as shown in FIG. 3G, and the inserting operation as shown in FIG. 3H are repeated in this order. Thereby, the insertion portion 12 can be inserted to a deeper portion in the intestinal tract 90.

When the balloons 60 and 80 are expanded as shown in FIG. 3F and FIG. 3G, the balloons 60 and 80 become spherical shapes with almost the same size. Therefore, the frictional resistances against the intestinal tract 90 become almost equal to each other between the balloons 60 and 80, whereby the intestinal tract 90 can be prevented from being pressurized when the insertion guide 70 is hauled in. Namely, in the case where the friction resistance on the first balloon 60 side is smaller than that on the second balloon 80 side, when the insertion guide 70 is hauled in, the insertion portion 12 does not come back and remains in the intestinal tract 90 and may pressurize the intestinal tract 90, and to the contrary, in the case where the friction resistance on the second balloon 80 side is smaller than that on the first balloon 60 side, when the insertion guide 70 is hauled in, the second balloon 80 slips off the intestinal tract 90 and the distance between the first balloon 60 and the second balloon 80 becomes longer and the balloons may pressurize the intestinal tract 90, however, according to this embodiment, since the friction resistances are almost equal to each other between the balloons 60 and 80, the intestinal tract 90 is prevented from being pressurized.

In this embodiment, the balloons 60 and 80 can be set to a friction resistance that enables the balloons to securely grasp the intestinal tract 90 while minimizing the pressurization on the intestinal tract 90. Namely, in this embodiment, by setting the friction resistances of the balloons 60 and 80 almost equal to each other, the friction resistances against the intestinal tract 90 can be minimized.

Furthermore, in this embodiment, the balloons are formed so as to expand to the same size by the same supplied pressure, so that when the intestinal tract 90 moves peristaltically, the balloons 60 and 80 contract by following the movement of the intestinal tract 90, and therefore, their friction resistances against the intestinal tract 90 are always constant, and this more securely prevents damage of the intestinal tract 90.

It is only required for the first balloon 60 and the second balloon 80 that their friction resistances against the intestinal tract 90 become equal to each other when they are expanded. Therefore, for example, it is allowed that the pressures supplied to the first balloon 60 and the second balloon 80 are different from each other.

The material of the first balloon 60 and the second balloon 80 is not limited to rubber, and other materials such as silicon can be selected. It is preferable that the first balloon 60 and the second balloon 80 are made of the same material, however, different materials may be selected as long as their frictional resistances become roughly equal to each other.

Figure 5A:
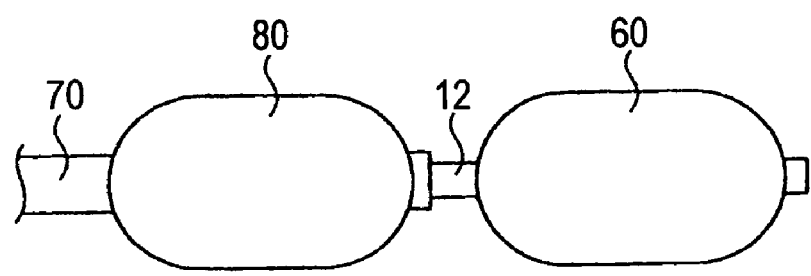
FIGS. 5A and 5B are side views of other shapes of the balloons.
Figure 5B:
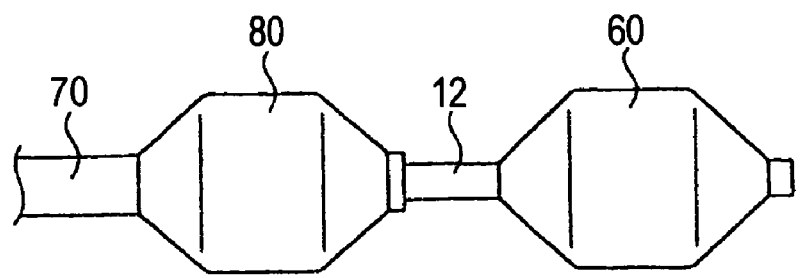

Furthermore, the shapes of the first balloon 60 and the second balloon 80 when they are expanded are not limited to the spherical shapes, and as shown in FIG. 5A, these may be ellipses long in the axial direction of the insertion portion 12 or the insertion guide 70. In addition, the shapes may be roughly cylindrical shapes including conical portions on both ends in the axial direction as shown in FIG. 5B. These shapes have circumferential surfaces and the surfaces come into contact with the intestinal tract 90, so that stable friction resistances are obtained. In addition, the first balloon 60 and the second balloon 80 are not limited to having shapes equal to each other, and may have different shapes as long as their friction resistances become roughly equal to each other.

It is preferable that the first balloon 60 and the second balloon 80 have the same size, the same shape, and the same coefficient of expansion not only when they are expanded but also in natural conditions. Thereby, the first balloon 60 and the second balloon 80 become the same shape regardless of the supplied pressures, so that their friction resistances always become equal to each other. In addition, in this case, the pressures to be supplied can be changed.

In the endoscope device and the control method for the same according to the invention, since the first balloon and the second balloon become equal to each other in friction resistance against the body cavity when they are expanded, when the balloons are expanded and the insertion portion and the insertion guide are pushed or pulled, the balloons can be prevented from pressurizing the body cavity, and therefore, an endoscope device which imposes a smaller burden on an examinee can be provided.

The entire disclosure of each and every foreign patent application from which the benefit of foreign priority has been claimed in the present application is incorporated herein by reference, as if fully set forth.

What is claimed is:

1. An endoscope device comprising:
   an endoscope including an insertion portion and a first balloon attached to a distal end of the insertion portion; and
   an insertion guide that is to be covered on the insertion portion to guide insertion of the insertion portion, the insertion guide comprising a second balloon on its distal end, wherein the insertion portion or the insertion guide is fixed in a body cavity by expanding the first balloon or the second balloon, respectively,
   wherein the insertion portion has a first insertion tube, and the insertion guide has a second insertion tube which is slidably coupled to the first insertion tube,
   a balloon controller that controls air pressure of the first and second balloons, wherein
   the balloon controller supplies air to each of the first and second balloons to expand each of the first and second balloons, and keeps an expanded states of each of the first and second balloons by controlling the air pressures thereof at constant values,
   the balloon controller suctions the air from each of the first and second balloons to contract each of the first and second balloons, and keeps a contracted states of each of the first and second balloons by controlling the air pressures thereof at constant values,
   the balloon controller controls the air pressures to become the same supply pressure between the first and second balloons so as to be substantially the same size between the first and second balloons,
   wherein the first balloon is detachable from an outer surface of the insertion portion, and
   wherein the first balloon and the second balloon are substantially equal to each other in friction resistance against the body cavity when they are expanded,
   at least one of the first and second balloons is formed into a roughly cylindrical shape narrowed on both ends thereof, and
   when supply pressures become substantially equal to each other for the first and second balloons for which internal pressures have values which are at least 26.7 hPa and at most 133.3 hPa, friction resistances for the first and second balloons become substantially equal to each other.

2. The endoscope device according to claim 1, wherein the first balloon and the second balloon comprise materials that are substantially equal to each other in friction resistance against the body cavity.

3. The endoscope device according to claim 1, wherein the first balloon and the second balloon comprise materials that are substantially equal to each other in coefficient of expansion.

4. The endoscope device according to claim 1, wherein the first balloon and the second balloon are substantially equal to each other in area to contact with the body cavity when they are expanded.

5. The endoscope device according to claim 1, wherein an air pressure is controlled by an air controller so that an outer diameter of the insertion portion is smaller than an outer diameter of the insertion guide, and a size of the first balloon is almost equal to a size of the second balloon.

6. The endoscope device according to claim 1, wherein the first balloon is attached on a top of the first insertion tube, and the second balloon is attached on a top of the second insertion tube.

7. The endoscope device according to claim 1, wherein the first insertion tube is connected to an air supply device through an operation portion and an air supply tube, and the second insertion tube is connected to the air supply device through a connecter and an air supply tube, respectively.

8. The endoscope device according to claim 1, further comprising fixing rings which are made of rubber and which are fitted on both ends of the first balloon.

9. The endoscope device according to claim 1, wherein,
connection portions exist between a controller main body and tubes for supplying and suctioning air to and from the first and second balloons, and
at said connection portions reflux preventive units are provided for preventing reflux of a body fluid when the first balloon or the second balloon bursts.

10. The endoscope device according to claim 1, wherein,
in an outer circumferential surface of the insertion portion where the first balloon is attached, a vent hole is formed,
the vent hole is communicated with a balloon air inlet formed in a hand-side control portion, and
the balloon air inlet is connected to the balloon controller via a first connecting tube.

11. The endoscope device according to claim 1, wherein,
a second connecting tube adhering to the outer circumferential surface of the insertion guide is communicated with the second balloon,
at the base end of the second connecting tube, a connector is provided,
the second connecting tube is connected to the connector, and the connector is connected to the balloon controller via the second connecting tube.

* * * * *